United States Patent [19]

Dyroff

[11] Patent Number: 5,324,880
[45] Date of Patent: Jun. 28, 1994

[54] PROCESS FOR DEHYDROGENATION OF PARAFFIN

[75] Inventor: David R. Dyroff, St. Louis, Mo.

[73] Assignee: Monsanto Company, St. Louis, Mo.

[21] Appl. No.: 919,628

[22] Filed: Jul. 24, 1992

Related U.S. Application Data

[63] Continuation of Ser. No. 533,323, Jul. 5, 1990, abandoned.

[51] Int. Cl.$^5$ ................................................. C07C 5/23
[52] U.S. Cl. ........................................................ 585/660
[58] Field of Search ........................................... 585/660

[56] References Cited

U.S. PATENT DOCUMENTS

| | | | |
|---|---|---|---|
| 3,274,287 | 9/1966 | Moore | 260/683.3 |
| 3,293,319 | 12/1966 | Abell, Jr. et al. | 260/683.3 |
| 3,315,007 | 4/1967 | Abell, Jr. et al. | 260/683.3 |
| 3,315,008 | 4/1967 | Abell, Jr. et al. | 260/683.3 |
| 3,448,165 | 6/1969 | Bloch | 260/683.3 |
| 3,458,592 | 7/1969 | Sen, III et al. | 260/683.3 |
| 3,527,836 | 9/1970 | Turner et al. | 260/683.3 |
| 3,551,574 | 12/1970 | Frohberger et al. | 424/311 |
| 3,576,766 | 4/1971 | Rausch | 252/439 |
| 3,585,253 | 6/1971 | Huang | 260/683.3 |
| 3,617,504 | 11/1971 | Berg | 585/660 |
| 3,632,662 | 1/1972 | Dyroff et al. | 260/683.3 |
| 3,647,719 | 3/1972 | Hayes | 252/466 |
| 3,649,566 | 3/1972 | Hayes et al. | 252/470 |
| 3,662,018 | 5/1972 | Parker | 260/683.3 |
| 3,761,531 | 9/1973 | Bloch | 260/668 |
| 3,767,594 | 10/1973 | Vesely | 252/439 |
| 3,792,110 | 2/1974 | Senn, III et al. | 585/660 |
| 3,825,612 | 7/1974 | Wilhelm | 260/668 |
| 3,907,921 | 9/1975 | Winter, III | 260/683.3 |
| 3,920,615 | 11/1975 | Huang | 260/683.3 |
| 3,998,900 | 12/1976 | Wilhelm | 260/668 |
| 4,048,245 | 9/1977 | Pollitzer et al. | 260/668 |
| 4,070,413 | 1/1978 | Imai | 260/683.3 |
| 4,125,565 | 11/1978 | Antos | 260/668 |
| 4,133,842 | 1/1979 | Anderson | 260/683.3 |
| 4,136,127 | 1/1979 | Antos | 260/668 |
| 4,172,583 | 10/1979 | Antos | 585/379 |
| 4,177,218 | 12/1979 | Antos | 585/379 |
| 4,216,346 | 8/1980 | Antos | 585/379 |
| 4,227,026 | 10/1980 | Flagg et al. | 585/434 |
| 4,268,706 | 5/1981 | Antos | 585/430 |
| 4,312,792 | 1/1982 | Antos | 252/466 |
| 4,341,664 | 7/1982 | Antos | 252/466 |
| 4,343,724 | 8/1982 | Antos | 252/466 |
| 4,396,540 | 8/1983 | Antos | 252/466 |
| 4,486,547 | 12/1984 | Imai et al. | 502/223 |
| 4,595,675 | 6/1986 | Imai et al. | 502/227 |
| 4,608,360 | 8/1986 | Abrevaya et al. | 502/226 |
| 4,677,237 | 6/1987 | Imai et al. | 585/444 |
| 4,827,072 | 5/1989 | Imai et al. | 585/443 |

Primary Examiner—Anthony McFarlane
Assistant Examiner—Nhat D. Phan
Attorney, Agent, or Firm—R. Loyer

[57] ABSTRACT

An improved process for dehydrogenation of detergent range normal paraffins contained in a hydrocarbon mixture to produce monoolefins is described. Improvements are obtained by operating over an entire catalyst operating cycle at an average added hydrogen to detergent range hydrocarbon ratio of from about 0.5 to about 1.9. The improved process is operated in a substantially adiabatic, plug flow reactor at a suitable catalyst bed inlet temperature not greater than about 450° C. The process provides improved tolerance for initial excess catalyst bed activity, allowing desirable catalyst operating cycle lengths to be obtained with more favorable operating conditions.

21 Claims, 2 Drawing Sheets

PROCESS FOR DEHYDROGENATION OF PARAFFIN

This is a continuation of application Ser. No. 07/533,323, filed on Jul. 5, 1990, now abandoned.

BACKGROUND OF THE INVENTION

The present invention relates to an improved process for the production of linear monoolefins by the catalytic dehydrogenation of the corresponding normal paraffins. More specifically, the invention relates to an improved process for the production of linear monoolefins containing from about 9 to about 15 carbon atoms per molecule. Such monoolefins, referred to herein as detergent range olefins, are particularly useful as reactive intermediates in the production of biodegradable detergents. This invention relates to specific combinations of reaction conditions different from those suggested by the prior art which have surprisingly been discovered to be quite advantageous for use with platinum catalysts in the production of detergent range olefins.

It is known that dehydrogenation processes employing noble metal catalysts are effective for the production of detergent range olefins, with catalysts comprising platinum being particularly effective. Rather broad ranges of reaction conditions which can be used in such processes are also known in the art. However, the production efficiency can vary widely depending upon the properties of the catalyst and the particular combination of reaction conditions selected.

It is known that in the catalytic dehydrogenation of normal paraffins, the percentage conversion to monoolefins in a single pass is subject to a severe equilibrium limitation. While the limiting conversion can vary considerably with the reaction conditions, the actual percentage of monoolefin in the products is typically not greater than about twenty weight percent of the total hydrocarbons present. It is also well known that the formation of monoolefins in such processes is accompanied by the formation of various less desirable by-products including diolefins, aromatics, and hydrocarbons with carbon numbers below the detergent range which are formed by cracking reactions. As used herein, the term "conversion" means the percentage of the normal paraffins in the feed which are converted in a single pass to species other than normal paraffins within the same carbon number range, and the term "selectivity" means the percentage of the converted normal paraffins which are converted to monoolefins within the same carbon number range. In cases in which the feed contains species other than normal paraffins within the desired carbon number range, these species are ignored in the calculation of conversion and selectivity. In general, higher conversion and higher selectivity are advantageous, but an increase in conversion tends to lower selectivity.

Another well known problem encountered in the production of detergent range olefins by catalytic dehydrogenation of normal paraffins is the loss of catalyst activity during its use. The catalyst can lose activity as a result of strong catalyst poisons such as sulfur in the feed, and such activity loss is generally controlled by controlling feed purity. But even when the feed contains extremely low levels of such poisons, the catalyst tends to deactivate at a significant rate due to the formation of coke on the catalyst surfaces. The rate of coke formation can vary widely depending upon the combination of reaction conditions selected. In general, a lower rate of coke formation is advantageous since this reduces various costs associated with catalyst regeneration or replacement and facilitates the maintenance of both conversion and reaction conditions within optimum ranges for extended periods of operation.

One method used in prior art paraffin dehydrogenation processes to reduce catalyst deactivation due to coke formation is to mix varying amounts of hydrogen with the vaporized paraffin feed prior to its introduction into the catalytic reaction zone. It is taught in U.S. Pat. No. 4,343,724 for example that such hydrogen serves a "dual-function" in both diluting the paraffin and "suppressing the formation of hydrogen deficient, carbonaceous deposits on the catalyst composite." In many cases, the amount of hydrogen used in patent examples has been extremely large, for example 4–8 moles of hydrogen per mole of hydrocarbon. Severe disadvantages accompany such large additions of hydrogen, including an adverse effect upon the equilibrium for monoolefin formation, increased size of most portions of the processing equipment for a given production rate, and increased energy and maintenance costs associated with the recovery, recompression, and recycle of hydrogen. Thus, it is greatly advantageous to reduce the hydrogen to hydrocarbon mole ratio ($H_2$:HC) used in the process. However, the prior art suggests that a $H_2$:HC ratio of at least about 2.0 is required to obtain favorable results.

Prior art teaching related to $H_2$:HC ratios and reaction temperatures for use in platinum catalyzed dehydrogenation of detergent range normal paraffins is illustrated in Table I. Unless otherwise noted, the $H_2$:HC ratios apply to the reactor feed mixture, and the temperatures are reactor inlet temperatures for use with a substantially adiabatic reactor. The broad ranges generally apply to a carbon number range wider than $C_9$–$C_{15}$. Preferred ranges may also apply to a wider carbon number range, but if more than one preferred range was mentioned, that most applicable to detergent range feedstocks, about $C_9$ to about $C_{15}$, was used in the table. All examples applicable to detergent range feedstocks were included under the heading of examples.

In Table I, the lowest $H_2$:HC ratio given in any example of an operable process is 2.0. In U.S. Pat. No. 3,274,287 there were a few examples with no added hydrogen, but these were included to illustrate the failure of the process under such conditions. Since the examples in any given patent should generally include the best known mode of operation, such teaching leads one to expect that the $H_2$:HC ratio must be at least 2.0 to obtain satisfactory results. Similarly, these teachings lead one to expect that the inlet temperature for a single stage adiabatic reactor would best be selected from a range of about 427° C. to about 575° C.

TABLE I

| | Prior Art Choices of $H_2$:HC Ratio and Temperature | | | | | |
|---|---|---|---|---|---|---|
| | $H_2$:HC Ratio Ranges | | | Temperature Ranges, °C. | | |
| U.S. Pat. No. | Broadest | Preferred | Examples | Broadest | Preferred | Examples |
| 4,827,072 | 0.1–20 | 1–10 | 4 | 200–1000 | 525–700 | 495 |

TABLE I-continued

| | Prior Art Choices of H2:HC Ratio and Temperature | | | | | |
| | H2:HC Ratio Ranges | | | Temperature Ranges, °C. | | |
| U.S. Pat. No. | Broadest | Preferred | Examples | Broadest | Preferred | Examples |
| --- | --- | --- | --- | --- | --- | --- |
| 4,677,237 | 0.1–40 | 1–10 | 4 | 400–900 | — | 495 |
| 4,608,360 | 0.1–40 | 1–10 | 4 | 400–900 | — | 495 |
| 4,595,673 | 0.1–40 | 1–10 | 4 | 400–900 | — | 495 |
| 4,551,575 | 1–40 | 1.5–10 | 6 | 400–900 | — | 485 |
| 4,486,547 | 1–40 | 1.5–10 | 6 | 400–900 | — | 485 |
| 4,396,540 | 1–20 | 1.5–10 | 4–5 | 371–704 | 427–510 | 443–454 |
| 4,343,724 | 1–20 | 1.5–10 | 4–5 | 371–704 | 427–510 | 443–454 |
| 4,341,664 | 1–20 | 1.5–10 | 4–5 | 371–704 | 427–510 | 443–454 |
| 4,312,792 | 1–20 | 1.5–10 | 4–5 | 371–704 | 427–510 | 443–454 |
| 4,268,706 | 1–20 | 1.5–10 | 4–5 | 371–649 | 427–510 | 443–454 |
| 4,227,026 | 1–20 | 1.5–10 | 4–5 | 371–649 | 427–510 | 443–454 |
| 4,216,346 | 1–20 | 1.5–10 | 4–5 | 371–649 | 427–510 | 443–454 |
| 4,177,218 | 1–20 | 1.5–10 | 8 | 375–650 | 375–550 | 465 |
| 4,172,853 | 1–20 | 1.5–10 | 8 | 371–649 | 427–510 | 443–460 |
| 4,136,127 | 1–20 | 1.5–10 | 5 | 371–649 | 427–510 | 449–460 |
| 4,133,842 | <15 | — | 7.5 | 399–566 | 427–510 | 460 |
| 4,125,565 | 1–20 | 1.5–10 | 4–5 | 371–649 | 427–510 | 443–454 |
| 4,070,413 | 1–20 | — | — | 400–700 | 450–550 | — |
| 4,048,245 | 1–20 | 1.5–10 | 5 | 371–649 | 427–510 | 438–454 |
| 3,998,900 | 1–20 | 1.5–10 | 8 | 371–677 | 427–510 | 449–466 |
| 3,920,615 | 0.1–50 | 1–5 | 2–8 | 400–650 | 420–520* | 430–450* |
| 3,907,921 | — | — | — | 430–540 | 460–485 | — |
| 3,825,612 | 1–20 | 1.5–10 | 8 | 371–649 | 427–510 | 449–466 |
| 3,767,594 | 1–10 | — | 8 | 399–704 | — | 460–475 |
| 3,761,531 | 1–20 | 5–15 | 8 | 371–649 | 427–510 | 443–475 |
| 3,662,018 | — | — | 8 | 427–510 | — | 454–460 |
| 3,649,566 | 1–20 | 1.5–10 | 8 | 371–677 | 427–510 | 449–466 |
| 3,647,719 | 1–20 | 1.5–10 | 8 | 371–677 | 427–510 | 449–466 |
| 3,632,662 | — | — | 2 | — | — | 452* |
| 3,585,253 | 0.1–50 | 1–5 | 2 | 400–650 | 420–520* | 450* |
| 3,576,766 | 1–20 | 1.5–10 | 8 | 371–677 | 427–510 | 449–466 |
| 3,527,836 | 0.1–30 | 2–10 | 4.1 | 400–650 | — | 440 |
| 3,458,592 | 0.5–15 | — | 5.5–7.8 | 427–510 | 454–488* | 454–460* |
| 3,448,165 | <15:1 | <10:1 | 2–8 | 400–700 | 430–530 | 427–575 |
| 3,315,008 | 0.1–5 | 1–3 | 2 | 400–650 | 520–520* | 435–440* |
| 3,315,007 | 0.1–5 | 1–3 | 2 | 400–650 | 520–520* | 440* |
| 3,293,319 | 1–10 | — | 4–8.8 | 400–700 | — | 430–460 |
| 3,274,287 | 0.5–5 | 1–3 | 2+ | 400–500 | 420–480* | 420–440* |

*Cited studies used an isothermal reactor
+Also includes examples of nonoperability at H2:HC = 0.

SUMMARY OF THE INVENTION

In accordance with this invention, there is provided an improved process for producing detergent range monoolefins by contacting the corresponding detergent range normal paraffins contained in a hydrocarbon mixture under dehydrogenation conditions with a dehydrogenation catalyst comprising platinum in a reaction system of one or more stages, the improvement comprising contacting said paraffins, in at least one included stage, with said catalyst in the presence of added hydrogen, said added hydrogen being in a molar ratio of hydrogen to total detergent range hydrocarbons in the mixture of from about 0.5 to about 1.9, said ratio being the average ratio maintained over the catalyst operating cycle. The improved process is operated in a substantially adiabatic, plug flow reactor at a suitable catalyst bed inlet temperature not greater than about 450° C.

In view of the prior art teaching of relatively high hydrogen to hydrocarbon ratios in examples described in patents noted above, it was quite surprising to discover that catalyst operating cycles in the process of this invention are not impractically short due to coke deposition as would be expected at the lower average ratios now taught. Cycles of acceptable length (i.e., two weeks or more) may be achieved at an average H2:HC ratio in the range of from about 0.5 to about 1.9 employed in accordance with this invention. This ability to operate at such low average H2:HC ratios results in a number of advantages, among the more important being the ability to use lower operating temperatures without loss of conversion of paraffin to product monoolefin. Because lower operating temperatures are now useful, the efficiency of the process increases in several ways. Particularly surprising is the increased tolerance to excess catalyst observed in the process of this invention which results in providing even longer catalyst operating cycles without the expected excessive reduction in selectivity of the dehydrogenation reaction. These and many other advantages of the improved process of this invention are described below.

DETAILED DESCRIPTION OF THE INVENTION

Figure 1:
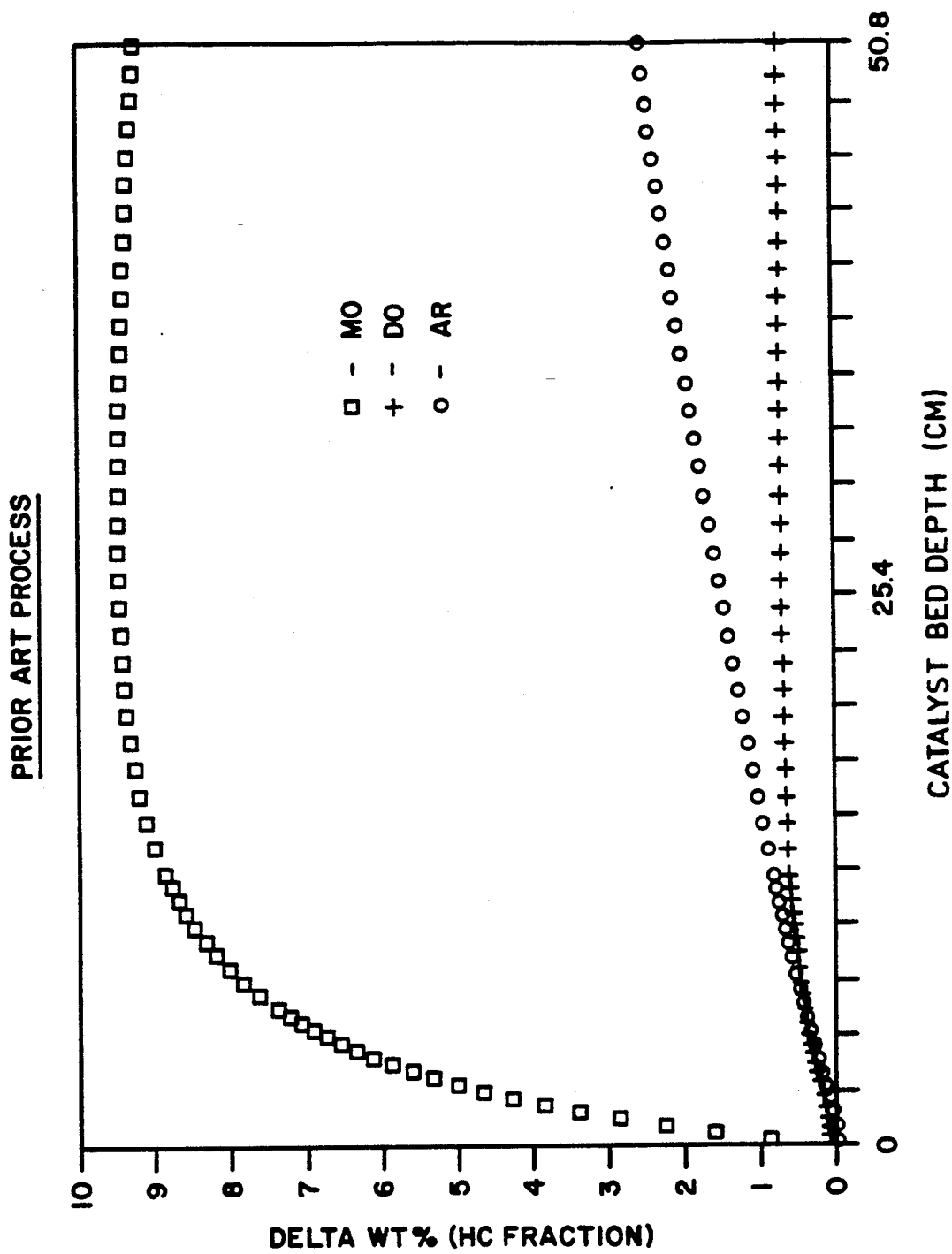
FIG. 1 is a graphical representation of calculated values based upon a kinetic model of a prior art process.

As employed herein, "substantially adiabatic" means that temperatures within a catalyst bed are determined primarily by the temperature of the mixture entering the catalyst bed and the extent of various chemical reactions occurring within the bed. "Substantially plug flow" means that a stage includes no device such as an agitator or recycle line for increasing the degree of back mixing of the reaction mixture. "Operated" means maintained at the specified operating conditions for a substantial fraction of the total operating time of a catalyst cycle. Neither the occurrence of such conditions as transients during startup, shutdown, or upsets, nor the use of such conditions for a brief catalyst breaking period or a brief period at the end of the catalyst's life is included within the definition of the word "operated" as used above.

The term "catalyst cycle" means herein the time interval between the time of start up of the process with new catalyst or newly regenerated catalyst to the time of shutdown for the purpose of regenerating or replacing the catalyst because of its loss of activity or deactivation as will be more particularly noted below.

As employed herein, the phrase "suitable catalyst bed inlet temperature" means a temperature selected to provide the desired balance among paraffin conversion, selectivity to monoolefin, and catalyst deactivation rate, to the extent allowed by the other reaction conditions. In each case, the suitable inlet temperature will depend in a complex manner upon the choices of the other conditions and the chosen targets for conversion, selectivity, and deactivation rate. However, once these other choices have been made, suitable catalyst bed inlet temperatures or sequences of such temperatures can be easily determined by routine experimentation by one skilled in the art in view of the present disclosure.

As employed herein, "hydrogen to hydrocarbon ratio" refers to the mole ratio of added hydrogen to total detergent range hydrocarbons fed to the system. Hydrogen generated by the process within the same pass is not included in added hydrogen. The process of this invention provides many significant advantages over processes suggested by the prior art. The lower $H_2$:HC ratios employed result in smaller volumetric flows and therefore reduced size and cost for processing equipment at a given production capacity. Energy costs for recompression and reheating of hydrogen are also reduced. In general, suitable reaction temperatures for use in the process of this invention are considerably lower than those suitable for use at higher $H_2$:HC ratios. One reason for this is that lower temperature and lower $H_2$:HC ratio have opposite effects upon the equilibrium which limits monoolefin formation. This ability to operate at lower temperatures results in a number of significant advantages.

Among the advantages of lower process temperatures are reduced yield loss to cracking reactions, lower energy costs, reduced coke formation rates, lower equipment maintenance costs, improved catalyst effectiveness, and increased tolerance for excess catalyst bed activity. By improved catalyst effectiveness is meant a reduction in the adverse effects of internal pore diffusion resistance upon the rate and selectivity of monoolefin formation. Dehydrogenation catalysts generally employ a porous support. While effectiveness can be varied in a number of ways, the effectiveness of any particular catalyst will tend to improve as operating temperature is lowered.

By increased tolerance for excess catalyst bed activity is meant a reduction in the extent to which reaction selectivity is degraded as catalyst bed activity is increased beyond the minimum amount required to reach the target monoolefin concentration in the product under a given set of conditions. A high tolerance for excess catalyst bed activity is very beneficial because it facilitates control of paraffin conversion, reduces yield losses resulting from unavoidable fluctuations in reaction conditions, and allows the length of processing cycles to be increased by using more excess catalyst activity at the beginning of a cycle without incurring unacceptably low selectivity early in the cycle.

One surprising aspect of the process of this invention, in view of the prior art teaching, is that processing cycles of practical length can be achieved when the $H_2$:HC ratio is below 2.0 for most or all of the cycle. While not bound by any theory, it appears that the expected adverse effect upon the coke formation rate of reducing the H2:HC ratio to a value within the 0.5–1.9 range of this invention can be significantly or in some cases possibly entirely offset by the retarding effect upon the coke formation rate of employing lower suitable catalyst bed inlet temperatures.

Another surprising aspect of the process of this invention is that it can provide such a high degree of tolerance for excess catalyst bed activity. While not bound by any theory, it appears that this is primarily due to two factors. First, the use of a lower catalyst bed inlet temperature in a substantially adiabatic plug flow reactor can provide such a low temperature in those portions of the catalyst bed downstream of the point of optimum conversion that the rate of various side reactions there is greatly reduced. And second, the lower $H_2$:HC ratio appears to have little or no accelerating effect upon those side reactions which significantly impact reaction selectivity.

Type of Normal Paraffins

The detergent range normal paraffins utilized as a feedstock in the present invention can be from any source and of any grade suitable for use in platinum catalyzed dehydrogenation. Included among such suitable feedstocks are single normal paraffins such as dodecane; mixtures of normal paraffins; normal paraffins produced by other processes, such as separation from kerosine by selective adsorption; unconverted paraffins separated within the dehydrogenation process and recycled for further conversion; paraffins containing varying levels of impurities such as non-normal paraffins, aromatics, or normal paraffins of carbon number outside the detergent range; paraffins admixed with their corresponding dehydrogenation products such as those found in the effluent from a previous dehydrogenation stage; and paraffins purified to varying degrees to remove catalyst deactivating impurities such as sulfur compounds or other objectionable impurities. Preferred paraffin properties include high content of the detergent range normal paraffins and low content of all impurities. The preferred range for the carbon number of the normal paraffins is from about 10 to about 14. It is preferred that the breadth of the carbon number distribution for a given feedstock should be about 4 carbons or less.

CATALYST

Any catalyst comprising platinum and suitable for dehydrogenation of detergent range normal paraffins can be used in the process of this invention. Catalysts employing a porous alumina support are preferred. Especially preferred are catalysts comprising platinum, copper, and an alkali metal upon a suitable porous alumina support as taught in U.S. Pat. No. 3,585,253 and U.S. Pat. No. 3,920,615. At the beginning of an operating cycle, the catalyst can be not previously used, previously used, or any mixture thereof. Previously used catalyst can be regenerated prior to reuse by any suitable procedure such as burning off accumulated coke.

Any effective means can be used for reducing the platinum to the zero oxidation state required for dehydrogenation. It is preferred to subject the platinum to reduction prior to the introduction of the hydrocarbon feed. If more than one reaction stage is used, the catalyst in different stages can be alike or different. Some catalysts may benefit from pretreatments such as presulfiding or from the use of special breaking conditions during their first use.

Type of Hydrogen

The hydrogen utilized in the present invention can be from any source and of any grade suitable for use in platinum catalyzed dehydrogenation of normal paraffins. Suitable types include hydrogen produced by another process; hydrogen generated within the dehydrogenation process, separated, and recycled; and hydrogen of varying purity. For economic reasons, it is usually preferred to use hydrogen generated within the process. The extent of purification or treatment of recycle hydrogen prior to its reuse should be selected to optimize overall process efficiency.

H2:HC Ratio and Use of Diluents

For the practice of this invention, the H2:HC ratio (based upon amounts fed to the process) should average in the range from about 0.5 to about 1.9 during the catalyst cycle. Within this range, the H2:HC ratio can be constant or varied within a catalyst cycle, and the optimum ratio will vary depending upon the other conditions, including the average molecular weight of the normal paraffins used. The optimum ratio for any particular situation can be determined by routine experimentation by one skilled in the art in view of the present disclosure. One of the effects of hydrogen in the feed mixture is dilution of the normal paraffins. The use of additional diluents such as steam, methane, carbon dioxide, nitrogen, and the like has been suggested in the prior art. While such diluents can be used in the practice of this invention, it is preferred not to deliberately add them. While not bound by any theory, it is generally believed that the effects of hydrogen go beyond simple dilution effects. In particular, hydrogen is believed to play a role in suppressing formation of coke upon catalyst surfaces and in maintaining the platinum in the necessary elemental metallic state. For most purposes, it is preferred to use an average H2:HC ratio in the range from about 0.8 to about 1.8 in the practice of this invention.

Reaction Temperature

For the practice of this invention, the inlet temperature for any catalyst bed should not exceed about 450° C. Below this limit, any inlet temperature suitable for platinum catalyzed dehydrogenation of detergent range normal paraffins can be used. The inlet temperature required for a particular reaction stage depends strongly upon the increase in conversion desired across the stage, the conversion desired at the outlet of the stage, the total pressure, and the H2:HC ratio, all of which interact to determine whether the temperature at the exit of the stage will be high enough to allow the desired conversion to be reached before further conversion is prevented by the effects of the reaction equilibrium. Within a processing cycle, inlet temperature of a bed can be constant or varied. For any particular situation, the optimum inlet temperature can be determined by routine experimentation by one skilled in the art in view of the present disclosure. It is preferred to use an inlet temperature just high enough to produce the desired conversion at the exit of a reactor. It is further preferred to select the other process parameters, including the number of stages and the final conversion, so that the inlet temperature of each stage can be not greater than about 440° C. When two or more stages are used, it is advantageous to use still lower inlet temperatures in the early stages. For example, in a first stage, an inlet temperature in the range of from about 340° to about 430° C. is preferred.

Total Pressure

Any total pressure suitable for the platinum catalyzed dehydrogenation of detergent range normal paraffins can be utilized in the practice of this invention. It is preferred that the pressure be at least one atmosphere because of extra costs and hazards associated with subatmospheric pressures. It is also preferred to use pressures below about three atmospheres because of chemical equilibrium advantages. It is especially preferred that pressures in a final reaction stage be as low as practicable, i.e. from about 1 atmosphere to about 1.68 atmospheres.

WHSV

The weight hourly space velocity (WHSV) is defined herein as the weight of normal paraffin feedstock entering a particular catalyst bed per hour per unit weight of catalyst in that bed (both weights being measured in the same units). As WHSV is increased, conversion across a catalyst bed of a given activity tends to decrease. Selecting a value of WHSV also fixes the value of such alternative parameters as liquid hourly space velocity (LHSV) or contact time. Any WHSV suitable for platinum catalyzed dehydrogenation of detergent range normal paraffins can be utilized in the practice of this invention. Values in the range from about 1 to about 20 are preferred. The best value for use in any particular situation can be determined by routine experimentation in view of the present disclosure.

Normal Paraffin Conversion

Any degree of conversion per pass and any means of controlling conversion which are suitable for the platinum catalyzed dehydrogenation of detergent range normal paraffins can be utilized in the practice of this invention. Conversion across one stage could be very low in some cases, for example about 1%. Total conversion across all stages of the dehydrogenation process could be as much as 18% or higher. The preferred range of normal paraffin conversion across all stages combined is from about 5% to about 15%. The best conversion for any particular case depends upon the other conditions in use including the molecular weight of the normal paraffins fed, and it can be determined by routine experimentation in view of the present disclosure. Conversion can be held within a narrow range during a processing cycle or allowed to vary widely as the catalyst deactivates. A narrow range of conversion is preferred, for example a range of two percentage points or less.

Suitable means of limiting the variation of conversion within a processing cycle include increasing reaction temperature or reducing the paraffin feed rate as catalyst activity declines, using reversible catalyst poisoning as described in U.S. Pat. No. 3,632,662, and intermittent or continuous replacement or addition of catalyst during processing. Any such means can be used in the practice of this invention. However, each of these means involves certain disadvantages. For example, when temperature is varied, part of the cycle typically is conducted at nonoptimal temperatures. When reversible poisoning is used, the activity of the catalyst is never as high as that for unpoisoned fresh catalyst. Variation of feed rate tends to create a need for more storage of in-process materials. And replacement or addition of catalyst during a processing cycle requires a more complex and costly reactor design. Because of such disadvantages, it is preferred to practice this invention without provision for catalyst replacement or addition during paraffin processing, without reversible catalyst poisoning, and without reliance upon large changes in paraffin feed rate or temperature within a processing cycle. Instead, it is preferred to begin processing cycles with a substantial excess of catalyst bed activity and select conditions within the ranges which characterize this invention which provide a high tolerance for excess catalyst activity. Excess initial catalyst bed activity can be defined as the percentage by which the initial catalyst bed activity exceeds that required at the end of a processing cycle to provide the desired minimum conversion under the conditions used at the end of the cycle. Using this definition, the amount of excess initial catalyst bed activity in the practice of this invention may be up to about 1000% or higher. In the usual practice of this invention, considering such factors as the length of the catalyst operating cycle, the desired upper limit of reaction temperature and the desired lower limit of reaction selectivity, the excess initial catalyst bed activity is in the range of from about 50% to about 500% and preferably in the range of from about 100% to about 300%.

Number and Type of Stages

The process of this invention can employ a single reaction stage or a plurality of stages. It is preferred to use either a single stage or two stages with a suitable reheating means between stages. If more than one stage is used, the reactor design and operating conditions for each stage can be alike or different and should be selected to optimize the efficiency of the total process. In a multistage system, one or more stages operated in accordance with this invention can be combined if desired with one or more stages operated under conditions not in accordance with this invention. It is preferred that all stages be operated in accordance with this invention.

Reactor Design

For the practice of this invention, the reactor or reactors employed should be designed for substantially adiabatic and substantially plug flow operation. One reason for this is that exposure of higher conversion reaction mixtures to hotter walls tends to lower reaction selectivity. Another reason is that exposure of such mixtures to the higher catalyst temperatures existing near the inlet of a substantially adiabatic reactor tends to both lower reaction selectivity and cause an unacceptably high rate of catalyst deactivation under the conditions of this process. Another reason is that selectivity tends to be highest when each increment of conversion occurs at the lowest possible average olefin to paraffin ratio, i.e. when back-mixing is minimized. A fourth reason is that the portion of an adiabatic reactor downstream of the region where most of the conversion occurs provides a favorable lower temperature environment for the preferred excess initial catalyst activity to reside.

As long as each reactor operated in accordance with this invention is substantially adiabatic and substantially plug flow, any other elements of reactor design suitable for use in platinum catalyzed dehydrogenation of detergent range normal paraffins can be utilized in the practice of this invention. The direction of flow can be down flow, up flow, or radial flow. The ratio of bed depth in the direction of flow to the bed cross sectional area at a particular depth can vary widely. The catalyst bed can be fixed or moving, but it cannot be fluidized since that would be incompatible with substantially plug flow operation.

It is preferred to use continuous, fixed bed, down flow cylindrical reactors with a ratio of length over diameter selected to minimize problems with wall effects, channeling, excessive back mixing, excessive thermal feedback, or insufficient turbulence outside the catalyst pellets. It is also preferred that the paraffin feed be completely vaporized and uniformly mixed with the hydrogen employed prior to contact with the catalyst bed.

Catalyst Cycles

The operation of a process with a particular catalyst bed from the time it is loaded or regenerated until it is removed or again regenerated is considered herein a catalyst cycle. The length of such a cycle refers to the time that was spent processing the feedstock and does not include idle periods. The length of a catalyst cycle can be varied widely. Shorter cycles tend to increase costs for new catalyst or reduce the percentage of time that a reactor is available for processing of paraffin. Longer cycles tend to make it more difficult to maintain conversion and operating conditions within optimum ranges as the catalyst deactivates. While any cycle length can be used, preferred cycle lengths are in the range from about two weeks to about six months. It is preferred that the entire operating cycle be conducted in accordance with the process of this invention.

Product Recovery and Use

The olefins produced by the process of this invention can be recovered or utilized in any suitable manner. Suitable uses include conversion to alkylbenzenes for use in detergents, conversion to various other products, and feeding to another dehydrogenation stage for further conversion of normal paraffins to olefins. Suitable methods of product recovery include various effective combinations of steps selected from condensation, gas-liquid separation, fractional distillation, selective adsorption, solvent extraction, and selective chemical reactions. In the preferred method, the gaseous reaction mixture generated by the process of this invention is cooled to produce a hydrocarbon rich liquid phase and a hydrogen rich gaseous phase. The gaseous phase is partly vented and partly recycled, with or without further refinement, to the dehydrogenation process. The liquid phase is optionally subjected to selective hydrogenation for conversion of diolefins to monoolefins and is in any case fractionated to remove low boiling cracking products. The remaining mixture comprising detergent range olefins and paraffins is contacted with benzene and an acidic catalyst under suitable alkylation conditions to convert the olefins mainly to alkylbenzene. The alkylation mixture is then separated by suitable means including fractional distillation into a product alkylbenzene fraction, an unconverted paraffin fraction, an unconverted benzene fraction, and other components such as recovered catalyst and various byproducts. The benzene and paraffin fractions are recycled, with or without further refinement or removal of purge streams, to the alkylation and dehydrogenation steps respectively. In a particularly preferred method, the acidic alkylation catalyst is hydrofluoric acid which is recovered from the alkylation mixture, at least partially purified, and recycled to the alkylation step.

The invention will be apparent from the processes shown in the following examples. These examples illustrate the process of this invention and are not to be regarded as limiting the scope of this invention.

EXAMPLE 1
KINETIC MODEL

A series of runs was carried out in a substantially gradientless recycle reactor under various dehydrogenation conditions with product samples collected at regular intervals. For each run, the catalyst was a previously unused sample taken from the same lot of a catalyst comprising about 2% copper, 0.47% platinum, and 0.3% potassium on an alumina support having a macropore volume of about 0.2 cc per gram and a surface area of about 200 square meters per gram. The catalyst particles were approximately spherical with U.S. standard sieve size $-6+7$ mesh. For each run, the feedstock was substantially identical containing about 0.45% normal undecane, 11.18% normal dodecane, 52.96% normal tridecane, 33.91% normal tetradecane, 0.12% aromatics, and 1.38% other species. Samples were analyzed by gas chromatography with a flame ionization detector without correction for any variations in response factor. Analyses from a given run during steady state operation were plotted against catalyst age, and the plots were extrapolated back to zero age to obtain estimates of the performance of fresh catalyst. The resulting estimates were used to calculate the rates of conversion of the $C_{11}-C_{14}$ normal paraffin fraction to the corresponding monoolefins and various byproducts under the various dehydrogenation conditions. This data was used to develop a kinetic model for prediction of the performance of an adiabatic, plug flow, fixed bed, dehydrogenation reactor containing fresh catalyst of the type described above. This model was then used as described below to compare the results obtainable using two sets of conditions, one in accordance with the improved process of this invention, the other being typical of the prior art.

The conditions selected for comparison were as follows:

TABLE II

|  | Improved Process | Prior Art |
| --- | --- | --- |
| Bed Inlet Temp. °C. | 432 | 451.7 |
| Bed Inlet Pressure ATM | 1.34 | 1.34 |
| H2:HC ratio | 1 | 4 |
| WHSV | 4.44 | 10.67 |
| Bed Depth cm. | 121.9 | 50.8 |
| Hydrogen Purity - % | 100 | 100 |

Figure 2:
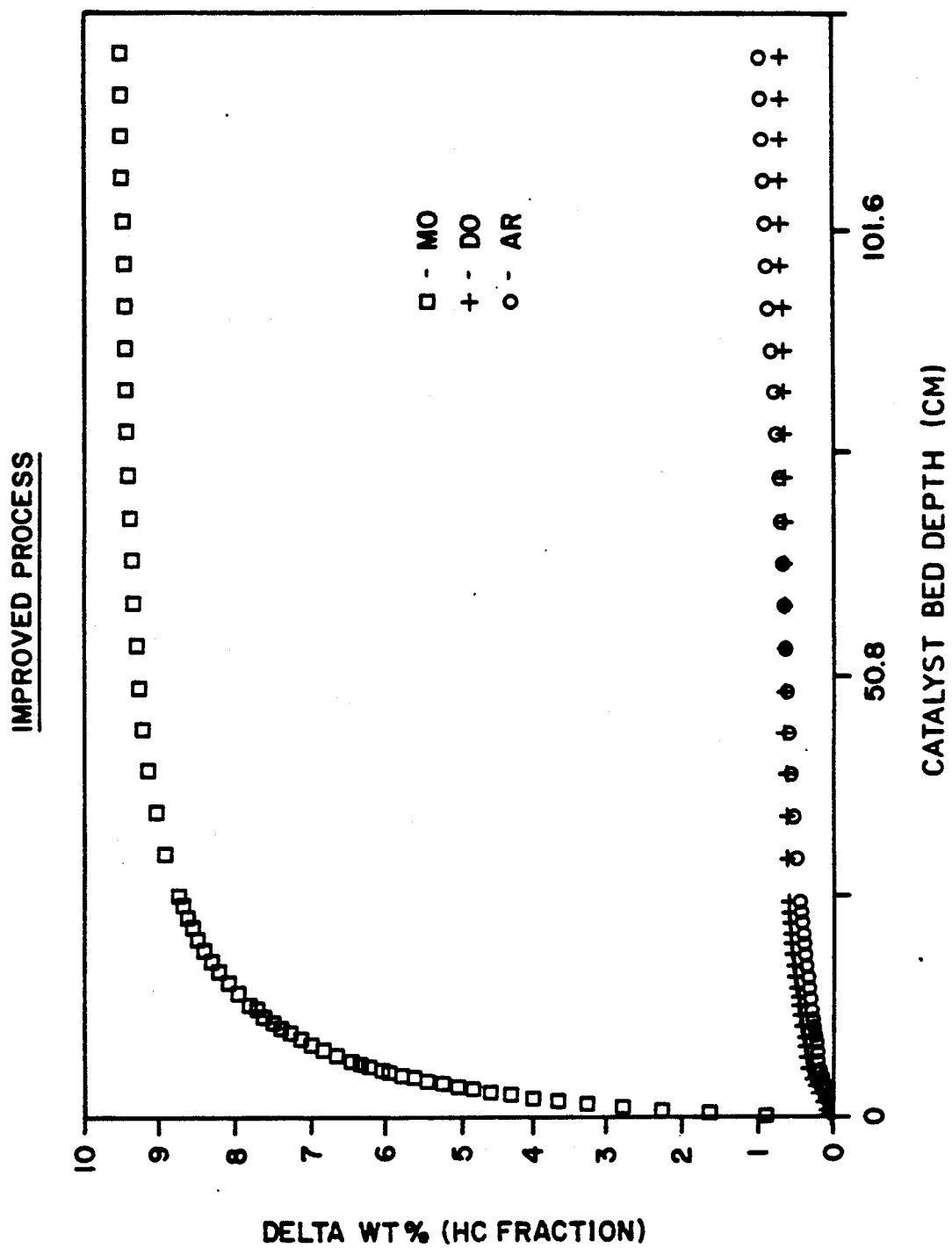
FIG. 2 is a graphical representation of calculated values based upon a kinetic model of the process of this invention.

The results calculated for the prior art process appear in FIG. 1. The results calculated for the improved process appear in FIG. 2. In both graphs the increases in the weight percentages of monoolefin (MO), diolefin (DO), and aromatics (AR) in the hydrocarbon fraction of the reaction mixture are plotted against distance from the feed end of the catalyst bed in centimeters.

Inlet pressure, hydrogen purity, and hydrocarbon feed rate (proportional to WHSV times bed depth) are the same in both cases. After selecting a value of 4.0 for the H2:HC ratio in the prior art case, the inlet temperature was adjusted to the value that resulted in the same maximum attainable MO formation (delta MO). As a result, points to the left of the peak MO position which have equal delta MO in the two cases are equivalent in their degree of approach to the steady state upper limit upon delta MO which is imposed by reaction equilibrium. To make the comparison still clearer, bed depth (and therefore WHSV as well) was reduced in the prior art case just sufficiently to cause 9.0% delta MO to occur at about the same horizontal distance from the left edge of the graph for both cases. This has no effect upon the coordinates of the points in units of centimeters of catalyst and component percentages.

In this embodiment of the improved process, at a bed depth of 29.5 cm where delta MO reaches 9.00%, the calculated selectivity to MO is 89.1%. As bed depth increases, delta MO keeps rising gradually. It reaches 9.47% at a bed depth of 109.7 cm, where the selectivity is 85.3%. This shows that under these conditions, if catalyst bed depth is 3.71 times the amount needed to reach 9.00% MO, the delta MO obtained in initial operation is 9.47% and selectivity is only 3.8% lower than that obtained when catalyst bed activity is just enough to reach 9.00% MO.

In the comparable embodiment of the prior art process with H2:HC ratio 4.0, delta MO reaches 9.00% at a bed depth of 13.7 centimeters and the selectivity at that point is 85.5 %. At 3.71 times this bed depth, delta MO is 9.24% and selectivity is 74.3%. In this case, the rise in delta MO ends at a catalyst amount only 2.09 times that needed for 9.0% MO, and at this point delta MO is 9.48% and selectivity is 80.02%.

These results illustrate several of the advantages of the process of this invention over prior art teaching. At the lower H2:HC ratio, the same MO level can be obtained at a temperature 19.4° C. lower, and with just enough catalyst activity to reach a target delta MO of 9.00%, selectivity to MO is higher by 3.6%. This improvement is mostly due to lower aromatics formation but is also partly due to reduced cracking at the lower temperature. When the catalyst amount is increased by a given factor over that needed to reach 9.00% MO, the adverse effect upon initial selectivity is much smaller for the process of this invention. This increased tolerance for excess catalyst bed activity is highly advantageous as a means of extending the length of catalyst cycles while avoiding undesirably low selectivity when the catalyst is fresh. Also avoided are undesirably low conversion and/or high operating temperatures when the catalyst is comparatively highly deactivated.

EXAMPLE 2

The catalyst for this example was the same as in Example 1 except that the pellet size distribution was broader with about 94% falling within the range $-5$ to $+7$ mesh. The feedstock was a mixture of fresh and recycle paraffin containing about 91.6% normal paraffins, 5.5 % aromatics, and 2.9% other species such as isoparaffins, cracking products, etc. The normal paraffins fraction of the feedstock consisted of about 0.5 % C9, 19.8% C10, 44.3% C11, 32.6% C12 and 2.8% C13.

A substantially adiabatic fixed bed reactor was used which was equipped with both termocouples and sample points along the length of the catalyst bed. Hydrogen generated by the process was collected and recycled. H2:HC ratio was calculated based upon the hydrogen content of the recycle hydrogen (which also contained small amounts of light hydrocarbons). Condensible fractions were collected for GC analysis.

The reactor was charged with fresh catalyst to a bed depth of about 121.9 centimeters and operated at constant conditions as follows: bed inlet temperature 437.8° C., bed inlet pressure 154 ATM, H2:HC ratio 1.0, and WHSV 4.44. The composition changes were measured across the entire reactor at the reaction times indicated below in Table III.

TABLE III

| Time(hours) | % Delta MO | % Delta AR |
|---|---|---|
| 62 | 7.09 | 0.11 |
| 66 | 7.15 | 0.04 |
| 108 | 7.12 | 0.29 |
| 118 | 7.08 | 0.27 |
| 142 | 7.10 | 0.02 |
| 166 | 7.06 | 0.21 |
| 190 | 7.09 | 0.24 |
| 214 | 7.13 | 0.44 |
| 240 | 7.18 | 0.02 |
| 262 | 7.14 | 0.23 |
| 310 | 7.12 | −0.19 |
| 334 | 6.83 | 0.12 |
| 358 | 7.15 | 0.68 |
| Mean | 7.10 | 0.19 |
| σ | 0.09 | 0.22 |

This data exhibits no significant downtrend in either delta MO or delta AR over a period of 358 hours at constant operating conditions. From this it is concluded that the rate of catalyst deactivation under these conditions is low enough to allow catalyst operating cycles of practical length to be run. About 14 hours into the run, catalyst temperatures at ten points within the reactor indicated that the endothermic reaction was substantially complete within about the first 25-30% of the bed length. About 302 hours into the run such readings indicated that the reaction was substantially complete within about the first 30-35% of the bed length. This is further evidence that the catalyst deactivation rate was low under these conditions. At the end of the run (358 hours), a series of samples was taken at different bed depths. Analyses of these samples showed that the reaction was complete within about the first 25-35% of the bed. Thus, a large amount of excess catalyst activity still remained when the run was ended at 358 hours, further confirming that acceptable catalyst cycle lengths can be achieved in the process of this invention. The absence of measurable changes in composition or temperature beyond about the first 35% of the catalyst bed in this run is in agreement with the results calculated in Example 1 for operation with a large excess of catalyst activity under the conditions of the process of this invention.

EXAMPLE 3

The catalyst for this example was the same as in Example 2. The feedstock was a mixture of fresh and recycle paraffin containing about 92.1% C9-14 normal paraffins, 5.4% aromatics, and 2.5 % other hydrocarbons. The C9-14 normal paraffin fraction consisted of about 0.1% C9, 0.7% C10, 1.9% C11, 14.1% C12, 53.2% C13 and 30.0% C14. A reactor similar to that used in Example 2 was charged with fresh catalyst to a bed depth of about 121.9 cm. and operated over a period of 668 hours at the following conditions: bed inlet temperature beginning at 437.7° C. and increased in steps of 2.7° C. to 451.6° C. over the course of the run, bed inlet pressure 1.6 ATM, H2:HC ratio 1.8, and WHSV 4.44. Product samples were analyzed by GC at regular intervals. For the entire run, average delta MO was 6.80% and average delta AR was 0.34%. At the end of the run, delta MO was 6.23% and delta AR was 0.24%. This example further illustrates the feasibility of operating for an extended period with an H2:HC ratio below 1.9.

EXAMPLE 4

The catalyst for this example was the same as in Example 2 except that it had been regenerated twice and therefore had somewhat lower initial activity. An extended run was carried out in which operations were alternated between a light feedstock like that in Example 2 and a heavy feedstock like that in Example 3. Conditions for the light feedstock were the same as in Example 2. Conditions for the heavy feedstock were the same as in Example 3 except that the bed inlet temperature was maintained at 437.7° C. or slightly lower. For the light feed operations, delta MO averaged about 7.0%, and for heavy feed operations it averaged about 6.4%. Such operations were continued for 2000 hours without regeneration of the catalyst. At the end of the period, excess catalyst activity was still present.

EXAMPLE 5

A reactor charged with excess platinum on alumina catalyst was operated with a detergent range normal paraffin feedstock which had been converted in an earlier dehydrogenation stage to 5.0% MO content. Conditions used were as follows: bed inlet temperature 436.1° C., bed inlet pressure 1.57 ATM, H2:HC ratio 2.5, bed depth 96.5 cm, and WHSV 4.44. The inlet temperature used resulted in a peak MO content of 8.9% which was reached about halfway through the bed. By the end of the bed, MO content had dropped to 8.4%. Aromatics content was increased by about 2.8% across the entire bed, with an approximately linear rise from the feed end to the discharge end. This result is very similar to that seen in Example 1 for operation at H2:HC ratio 4.0. This illustrates further both the accuracy of the kinetic model used in Example 1 and the severe overreaction problems experienced when a large excess of catalyst activity is used under prior art conditions.

EXAMPLE 6

The catalyst for this example was the same as in Example 2 except that it had been regenerated seven times and therefore had considerably lower initial activity. The feedstock and conditions were essentially the same as in Example 2 except that the H2:HC ratio was 0.5 and the bed inlet temperature was set initially at 423.8° C. and increased during the run to 429° C. Operation was continued for 72 hours at these conditions, and product samples were analyzed by GC. Average delta MO was 6.68%.

What is claimed is:

1. A process for the catalytic dehydrogenation of detergent range normal paraffins contains in a hydrocarbon mixture to produce monoolefins by contacting said paraffins in admixture with added hydrogen in one or more substantially adiabatic, plug flow reaction stages with a platinum dehydrogenation catalyst under dehydrogenation conditions, wherein the catalyst is replaced or regenerated at intervals selected to provide a catalyst cycle, comprising providing an amount of said catalyst at the beginning of said cycle which is in the range of from about 100% to about 1000%, by weight, in excess of the amount required in the absence of catalyst deactivation to provide the conversion utilized at the end of said cycle, said process being operated at a molar ratio of added hydrogen to total detergent range hydrocarbons in said mixture in the range of from about 0.5 to about 1.9, said contacting occurring at suitable catalyst bed inlet temperatures of not greater than about 450° C. during the entire catalyst cycle, whereby the catalyst cycle length is substantially increased due to tolerance of said excess catalyst and said tolerance is provided by the combination of said hydrogen to hydrocarbon ratio and said limitation of bed inlet temperature.

2. The process of claim 1 wherein the catalyst is supported on a porous support.

3. The process of claim 2 wherein the hydrogen to hydrocarbon ratio is in the range of from about 0.8 to about 1.8.

4. The process of claim 2 wherein the detergent range normal paraffins have a carbon chain length of from about 10 to about 14 carbon atoms.

5. The process of claim 2 wherein the process comprises a plurality of stages and the hydrogen to hydrocarbon ratio in each stage is independently selected from the range of from about 0.5 to about 1.9.

6. The process of claim 2 wherein the normal paraffins are a mixture of fresh and recycled normal paraffins.

7. The process of claim 2 wherein the inlet temperature is not greater than about 440° C.

8. The process of claim 5 wherein the pressure in the final reaction stage is in the range of from about 1 to about 1.68 atmospheres.

9. The process of claim 5 wherein the total number of stages is two.

10. The process of claim 5 wherein the conversion of normal paraffin across all stages combined is in the range of from about 5% to about 15%, by weight, of said paraffin contained in said hydrocarbon mixture.

11. The process of claim 2 wherein the catalyst is in a single stage, continuous, fixed bed reactor.

12. The process of claim 2 wherein the weight hourly space velocity is in the range of from about 1 to about 20.

13. The process of claim 2 wherein the catalyst support is porous alumina.

14. The process of claim 13 wherein the catalyst comprises copper, platinum and alkali metal.

15. The process of claim 14 wherein the alkali metal is potassium.

16. The process of claim 2 wherein said excess catalyst bed activity at the beginning of said cycle is in the range of from about 100% to about 300%.

17. A process for the catalytic dehydrogenation of detergent range normal paraffins contained in a hydrocarbon mixture to produce monoolefins by contacting said paraffins in admixture with added hydrogen in one or more substantially adiabatic, plug flow reaction stages with a catalyst comprising an alumina support impregnated with a mixture comprising platinum, copper, and an alkali metal, under dehydrogenation conditions, wherein the catalyst is replaced or regenerated at intervals to provide a catalyst cycle, comprising providing an amount of said catalyst at the beginning of said cycle which is in the range of from about 100% to about 300%, by weight, in excess of the amount required in the absence of catalyst deactivation to provide the conversion utilized at the end of said cycle, said process being operated at a molar ratio of added hydrogen to total detergent range hydrocarbons in said mixture in the range of from about 0.8 to about 1.8, said paraffins having from about 10 to about 14 carbon atoms, said contacting occurring at a weight hourly space velocity of from about 1 to about 20 and at suitable catalyst bed inlet temperatures of not greater than about 440° C. during the entire catalyst cycle, whereby the catalyst cycle length is substantially increased without loss of yield due to increased tolerance of said excess catalyst and said tolerance is provided by the combination of said hydrogen to hydrocarbon ratio and said limitation of bed inlet temperatures.

18. The process of claim 17 wherein the alkali metal is potassium.

19. The process of claim 17 wherein the pressure in the final reaction stage is in the range of from about 1 to about 1.68 atmospheres.

20. The process of claim 17 wherein the process is operated in two stages.

21. The process of claim 20 wherein the inlet temperature of the initial stage is in the range of from about 340° C. to about 430° C.

* * * * *